(12) United States Patent
Miyata et al.

(10) Patent No.: US 7,807,657 B2
(45) Date of Patent: Oct. 5, 2010

(54) SEPARATE TYPE MEDICAL MATERIAL

(75) Inventors: Yoshiaki Miyata, Tokyo (JP); Yasukazu Himeda, Tokyo (JP); Masamichi Hashimoto, Tokyo (JP); Toshihiko Umeda, Tokyo (JP); Teruzou Miyoshi, Tokyo (JP)

(73) Assignee: Denki Kagaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/027,365

(22) Filed: Feb. 7, 2008

(65) Prior Publication Data

US 2008/0132585 A1 Jun. 5, 2008

Related U.S. Application Data

(63) Continuation of application No. 10/524,785, filed as application No. PCT/JP02/08328 on Aug. 16, 2002, now abandoned.

(51) Int. Cl.
*A01N 43/04* (2006.01)
*A61K 31/715* (2006.01)

(52) U.S. Cl. ..................................... 514/54
(58) Field of Classification Search ............... None
See application file for complete search history.

(56) References Cited

U.S. PATENT DOCUMENTS

| 4,582,865 A | 4/1986 | Balazs et al. |
| 4,605,691 A | 8/1986 | Balazs et al. |
| 4,713,448 A | 12/1987 | Balazs et al. |

FOREIGN PATENT DOCUMENTS

| EP | 0 341 745 | 12/1994 |
| EP | 0 216 453 | 3/1996 |
| JP | 2-234689 | 9/1990 |
| JP | 8-104642 | 4/1996 |
| JP | 8-143459 | 6/1996 |
| JP | 10-212303 | 8/1998 |
| JP | 11-302197 | 11/1999 |
| JP | 2001-129073 | 5/2001 |
| JP | 2001-278791 | 10/2001 |
| JP | 2002-35126 | 2/2002 |
| JP | 2002-348243 | 12/2002 |
| KR | 2001-89882 | 10/2001 |
| KR | 2005-7002440 A | * 9/2005 |
| WO | 63-123392 | 5/1988 |
| WO | 95/25751 | 9/1995 |
| WO | 97/49412 | 12/1997 |
| WO | 99/10385 | 3/1999 |
| WO | 99/15150 | 4/1999 |
| WO | 01/57093 | 8/2001 |

OTHER PUBLICATIONS

[R] O'Neil et al. (eds.), The Merck Index, An Encyclopedia of Chemicals, Drugs, and Biologicals, 13th Editions, 2001, Merck & Co., Whitehouse Station, NJ, only p. 849 supplied, see entry 4776 (hyaluronic acid).*
(S) Swinyard et al., "Pharmaceutical Necessities," Chapter 66 in Remington's Pharmaceutical Sciences, 18th Ed., Gennaro et al. (eds.), 1990, Mack Publishing Co, Easton, PA, only pp. 1286, 1303-1304 and 1317-1329 supplied.*
Seikagaku Data Book 1,The Japanese Biochemical Society, Tokyo Kagaku Dozin Co., LTD., p. 1569 (1979).
Ciba Foundation Symposium 143, The Biology of Hyaluronan, John Wiley & Sons, p. 265 (1989).

* cited by examiner

*Primary Examiner*—Lawrence E Crane
(74) *Attorney, Agent, or Firm*—Oblon, Spivak, McClelland, Maier & Neustadt, L.L.P.

(57) ABSTRACT

A separate type medical material containing a hyaluronic acid ester derivative, which satisfies the storage stability of a hyaluronic acid ester derivative and avoidance of irritation and pain at the time of injecting a therapeutic agent for joints, is provided. A separate type medical material comprising liquid (A) which is an aqueous solution containing a hyaluronic acid ester derivative and buffered to a pH of from 4.5 to 6.5, and liquid (B) which is an aqueous solution having such a buffering power that when it is mixed with the liquid (A), the mixed liquid has a pH within a range of from 6.8 to 7.8, kept separately from each other.

12 Claims, 1 Drawing Sheet

SEPARATE TYPE MEDICAL MATERIAL

This is a continuation application of U.S. application Ser. No. 10/524,785, filed Aug. 10, 2005, now abandoned, which is a 371 of PCT/JP02/08328 filed on Aug. 16, 2002.

TECHNICAL FIELD

The present invention relates to an injection for treating arthropathy employing a biocompatible hyaluronic acid ester derivative.

BACKGROUND ART

Hyaluronic acid is a linear macromolecular polysaccharide consisting of alternately bonded β-D-N-acetylglucosamine and β-D-glucuronic acid. Hyaluronic acid is found not only in connective tissues of mammals but also in cockscombs and the capsules of Streptococci. Hyaluronic acid is obtainable not only by extraction from cockscombs and umbilical cords, but also as purified products from the culture broth of Streptococci.

Natural hyaluronic acid is polydisperse in respect of molecular weight and is known to show excellent biocompatibility even when implanted or injected into the body by virtue of the absence of species and organ specificity.

Synovial fluid supplies nutrition to the articular cartilage and has incomparable functions as a lubricant and a shock absorber in the joint, and its excellent viscoelasticity heavily owes to one of the main components in the synovial fluid, hyaluronic acid. Hyaluronic acid is known to have a high molecular weight of from several million to ten million.

Concentration and molecular weight analyses of hyaluronic acid in the synovial fluid from patients with arthropathy such as osteoarthritis and chronic articular rheumatism demonstrated the concentration and molecular weight of hyaluronic acid in the synovial fluid from patients with arthropathy generally tend to lower than in normal synovial fluid, and it is considered that the lower concentration and molecular weight of hyaluronic acid are closely associated with development of locomotor dysfunction and pain attributable to the weaker lubricating action and the weaker protecting action on the surface of the articular cartilage of synovial fluid.

Injection of a hyaluronic acid solution into diseased joints has been adopted as an effective measure for knee osteoarthritis among those articular diseases. As examples of a therapeutic agent for knee joints, Artz (manufactured by Seikagaku Corporation, average molecular weight 900,000), Hyalgan (manufactured by Fidia, average molecular weight <500,000), or Suvenyl (manufactured by Aventis Pharma Ltd., CHUGAI PHARMACEUTICAL CO., LTD. and DENKI KAGAKU KOGYO KABUSHIKI KAISHA, average molecular weigh 1,900,000) which has been developed by the present inventors, with the idea that a higher effect can be expected with a higher molecular weight, which is also adapted to chronic articular rheumatism, may be mentioned.

Further, Synvisc (Genzyme) containing a crosslinked hyaluronic acid gel, in which hyaluronic acid is chemically crosslinked to make it have a high molecular weight, thereby to improve the viscoelasticity, has been developed. The crosslinked hyaluronic acid gel is a hyaluronic acid gel formed by chemically crosslinking hyaluronic acid with a crosslinker divinyl sulfone and is called Hylan. Methods for producing Hylan and a gel obtained by crosslinking Hylan are disclosed in U.S. Pat. No. 4,713,448 in detail. Single and mixed gels comprising hyaluronic acid as the base are disclosed in U.S. Pat. No. 4,582,865 and U.S. Pat. No. 4,605,691.

For treatment employing such preparations for joints, direct injection to the joints of patients 3 to 5 times every week is required, and decrease in the number of injections has been desired in view of the burden on the patients and doctors.

A therapeutic agent for joints containing self-crosslinking hyaluronic acid is also disclosed in WO97/49412. The object is to control viscoelastic properties and to prolong the residence time in the joint by crosslinking hyaluronic acid. A technique to control the viscoelasticity by uniformly mixing self-crosslinking hyaluronic acid and an aqueous solution of hyaluronic acid is disclosed. It is also conceptually disclosed that self-crosslinking hyaluronic acid is hydrolyzed in the articular cavity and can become natural hyaluronic acid containers (reservoirs).

The pH of the synovial fluid is from about 7.3 to about 7.6. It is pointed out that a pH of a therapeutic agent for joints to be injected into the articular cavity which is significantly different from the pH of the synovial fluid may cause irritation or pain (SEIKAGAKU DATA BOOK I, THE JAPANESE BIOCHEMICAL SOCIETY, TOKYO KAGAKU DOZIN CO., LTD., 1979, p 1569). Accordingly, the pH of Artz and Suvenyl is adjusted to be within a range centering on 7.4.

The form of distribution has been greatly changed from vial preparations to kit preparations such as prefilled syringes, also with respect to the therapeutic agent for joints, for the purpose of labor-saving at the time of preparation for administration at a medical institution and preventing bacterial contamination and contamination by foreign substances. It takes long to fill a syringe with a particularly highly viscous hyaluronic acid preparation by suction, and the amount in the syringe significantly fluctuates. Kit preparations are shown to be a medically effective form, with which the burden of preparation for administration at a medical institution is reduced and at the same time, a set amount of the liquid can be easily and more uniformly injected.

In the process of extensive studies on properties of a hyaluronic acid ester derivative, particularly self-crosslinking hyaluronic acid, the present inventors have found that the ester derivative has no adequate stability in a neutral region. A medical material to be administered to the body is prepared to be in a neutral region as a biological condition, however, a possibility is considered that when a hyaluronic acid ester derivative is adapted as a medical material under such a condition, it can not be stored for a long time in the process of e.g. distribution.

Accordingly, particularly for preparation of a medical material comprising such a hyaluronic acid ester derivative, in order to overcome such a problem that the hyaluronic acid ester derivative is unstable in a neutral pH region, the present inventors have been conducted extensive studies on a method for stably providing such an ester derivative. As a result, they have found that the ester derivative has a higher stability under a weakly acidic condition in a pH region of from 4.5 to 6.5. Further, they have conceived, to provide a medical material comprising a hyaluronic acid ester derivative as a component, such a preparation that a dispersed aqueous solution of a weakly acidic hyaluronic acid ester derivative and a neutralizing agent solution therefor, including a case where hyaluronic acid is dissolved in the neutralizing agent solution, are packed separately from each other so that they are under different pH conditions, they can be mixed for injection at the time of treatment, and finally they can be administered under a physiologic neutral pH condition, and they have accomplished the present invention.

DISCLOSURE OF THE INVENTION

The present invention provides:

(1) A separate type medical material, characterized in that it comprises liquid (A) which is an aqueous solution containing a hyaluronic acid ester derivative and buffered to a pH of from 4.5 to 6.5, and liquid (B) which is an aqueous solution having such a buffering power that when it is mixed with the liquid (A), the mixed liquid has a pH within a range of from 6.8 to 7.8, and the liquid (A) and the liquid (B) are kept separately from each other before administration and administered as mixed.

(2) The separate type medical material according to (1), wherein the hyaluronic acid ester derivative in the liquid (A) is self-crosslinking hyaluronic acid.

(3) The separate type medical material according to (1) or (2), wherein the aqueous solution containing a hyaluronic acid ester derivative as the liquid (A) has a concentration of the hyaluronic acid ester derivative of from 1 to 20 mass %.

(4) The separate type medical material according to (1), (2) or (3), wherein the liquid (B) which is an aqueous solution having such a buffering power that when it is mixed with the liquid (A), the mixed liquid has a pH within a range of from 6.8 to 7.8, is an aqueous solution having hyaluronic acid dissolved therein.

(5) The separate type medial material according to any one of (1) to (4), which further contains a medicine or a pharmaceutically acceptable lubricant.

(6) The separate type medical material according to (5), wherein the medicine or the pharmaceutically acceptable lubricant is dissolved or dispersed in the liquid (A) which is an aqueous solution containing a hyaluronic acid ester derivative and buffered to a pH of from 4.5 to 6.5.

(7) The separate type medical material according to (5) or (6), wherein the medicine or the pharmaceutically acceptable lubricant is dissolved or dispersed in the inside of the hyaluronic acid ester derivative in the liquid (A).

(8) The separate type medical material according to any one of (5) to (7), wherein the medicine or the pharmaceutically acceptable lubricant is dissolved or dispersed in the liquid (B) which is an aqueous solution having such a buffering power that when it is mixed with the liquid (A), the mixed liquid has a pH within a range of from 6.8 to 7.8.

(9) The separate type medical material according to any one of (5) to (8), wherein the pharmaceutically acceptable lubricant is a phospholipid.

(10) The separate type medical material according to any one of (1) to (9), which is a medical material for joint injection comprising the liquid (A) and the liquid (B) packed in a syringe separately from each other.

(11) A method of administering a medical material for a arthropathy, which comprises mixing liquid (A) and liquid (B) constituting the separate type medical material as defined in any one of (1) to (10) immediately before administration, and injecting the resulting mixed liquid to the joint of a patient for administration.

EXPLANATION OF SYMBOLS

Figure 1:
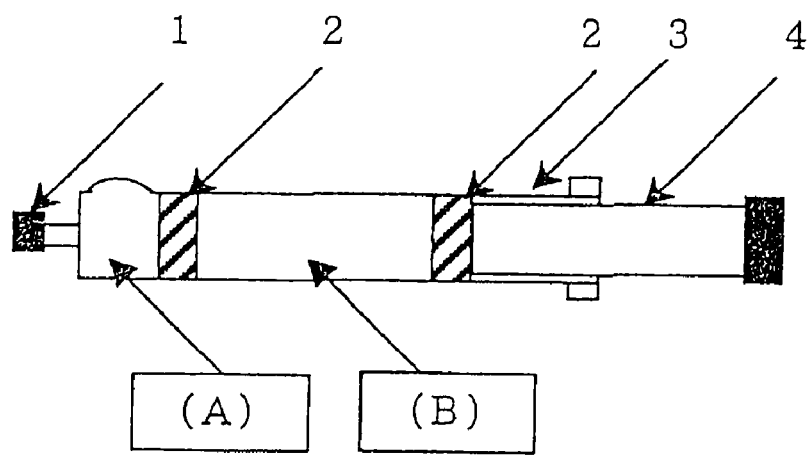
FIG. 1: A schematic view illustrating a sample packed in a prefilled syringe, as one embodiment of the separate type medical material of the present invention.

1: Component for sealing the tip
2: Rubber stopper
3: Cylinder
4: Plunger rod
(A): Gel suspension
(B): Hyaluronic acid solution

BEST MODE FOR CARRYING OUT THE INVENTION

Now, the present invention will be explained in detail below.

In the present invention, hyaluronic acid obtained by extraction from animal tissues or by fermentation may be used without any restriction on its source.

The strain used in fermentation is preferably a hyaluronic acid-producing microorganism isolated from nature such as the genus *Streptococcus* or a mutant which steadily produces hyaluronic acid in high yield such as *Streptococcus equi* FM-100 (accession number 9027 given by National Institute of Bioscience and Human-Technology) disclosed in JP-A-63-123392 or *Streptococcus equi* FM-300 (accession number 2319 given by National Institute of Bioscience and Human-Technology) disclosed in JP-A-2-234689. Pure hyaluronic acid obtained from cultures of the above-mentioned mutants may be used.

The molecular weight of the hyaluronic acid to be used in the present invention is preferably within a range of from about $1 \times 10^5$ to about $1 \times 10^7$ Da. Hyaluronic acid having a higher molecular weight may also be used after the molecular weight is lowered into this range by treatment such as hydrolysis.

In the present invention, the concept of hyaluronic acid is used so as to include its alkali metal salts such as sodium, potassium and lithium salts, too.

As the hyaluronic acid ester derivative and its production method, hyaluronic acid esters having a part of or the entire carboxyl groups esterified with aliphatic, aromatic, arylaliphatic (arylaliphatic), cycloaliphatic or heterocyclic series alcohols are disclosed in EP 0216453 B1. Further, self-crosslinked hyaluronic acid esters having a part of or the entire carboxyl groups esterified with alcohol groups on the same polysaccharide chain or a different polysaccharide chain are disclosed in EP 0341745 B1. Further, crosslinked compounds of hyaluronic acid having a part of or the entire carboxyl groups esterified with polyhydric alcohols of aliphatic, aromatic, arylaliphatic, cycloaliphatic or heterocyclic series, which underwent crosslinking by the spacer chain, are disclosed in EP 0265116 B1. Further, succinic acid hemiesters with hyaluronic acid or a partial or total ester of hyaluronic acid are disclosed in WO95/25751. Further, a gel of self-crosslinked hyaluronic acid, which is obtained by adjusting a hyaluronic acid aqueous solution to an acidic condition, and freezing and thawing the aqueous solution at least once, is disclosed in WO99/10385. Further, self-crosslinked hyaluronic acid formed by mixing hyaluronic acid and an acidic aqueous solution at a concentration of at least 5 mass % and keeping their coexistence, without freezing, is disclosed in WO01/57093. It is disclosed that the residual properties in the body improve when hyaluronic acid is formed into an ester derivative as compared with an aqueous solution of hyaluronic acid.

When an ester derivative of hyaluronic acid is used for a therapeutic agent for joints, an ester derivative of ester-crosslinked hyaluronic acid is preferred for the purpose of controlling viscoelastic properties. An ester of a polyhydric alcohol with the carboxyl group of hyaluronic acid, an ester of a polyhydric carboxylic acid with the hydroxyl group of hyaluronic acid, or self-crosslinked hyaluronic acid formed by ester linkage between the carboxyl group and the hydroxyl group of hyaluronic acid, is preferred. For the purpose of obtaining natural hyaluronic acid containers (reservoirs) by hydrolysis of the ester linkage in the articular cavity, preferred is ester-crosslinked hyaluronic acid, which has a low degree of esterification and of which the residual properties in the body are significantly changed.

As for the safety of the self-crosslinked hyaluronic acid, natural hyaluronic acid discharged by decomposition of the self-crosslinked hyaluronic acid, which is metabolized in the physiologic metabolic pathway, may be safer than ester-crosslinked hyaluronic acid, produced by another crosslinking reaction.

When an ester derivative of hyaluronic acid is used for a therapeutic agent for joints, when the object is to obtain natural hyaluronic acid containers (reservoirs), the molecular weight of hyaluronic acid itself to be discharged is preferably high. It has been known that the metabolism (transport) of hyaluronic acid from the articular cavity is greatly influenced by the molecular weight of hyaluronic acid itself (Ciba Foundation Symposium 143, The Biology of Hyaluronan, John Wiley & Sons, 1989, p 265).

If the molecular weight of discharged hyaluronic acid is at most about 300,000, the discharged hyaluronic acid is quickly metabolized (transported) from the articular cavity, and accordingly the effect of joint treatment may significantly decrease.

Then, the ester derivative of hyaluronic acid is used for a therapeutic agent for joints, it is injected into the articular cavity by means of an injection needle, and accordingly the ester derivative of hyaluronic acid has to be in the form of a suspension in which it is dispersed in a physiologically acceptable medium. The suspension may be prepared by grinding the ester derivative of hyaluronic acid by means of a grinder such as a mixer or a homogenizer at any stage of its production step and purification step. The dispersed particle size of the ester derivative of hyaluronic acid may optionally be adjusted to control physicochemical properties and effects of the therapeutic agent for joints. The dispersed particle size can be easily adjusted to from 0.05 mm to 2.0 mm by dispersing the ester derivative of hyaluronic acid in a physiologically acceptable medium and then treating the suspension with a homogenizer.

Ester-crosslinked hyaluronic acid swells in a physiologically acceptable medium and becomes a gel. The equilibrium swelling ratio of the gel may optionally be adjusted by the degree of crosslinking of the ester-crosslinked hyaluronic acid. For example, in a case where the equilibrium swelling ratio is 100 times, the hyaluronic acid concentration in the physiologically acceptable medium is 1.0 mass %. In a case where the equilibrium swelling ratio is 10 times, the hyaluronic acid concentration in a physiologically acceptable medium is 10 mass %. When the ester-crosslinked hyaluronic acid is used for the therapeutic agent for joints, when the object is to obtain natural hyaluronic acid containers (reservoirs), a higher therapeutic effect can be expected when the hyaluronic acid concentration in the physiologically acceptable medium is high, since the amount of hyaluronic acid to be injected into the articular cavity can be increased, assuming that the volume to be injected into the articular cavity is constant.

The hyaluronic acid concentration of a hyaluronic acid aqueous solution of a commercially available therapeutic agent for knee joints, such as Artz or Suvenyl, is 1.0 mass %. If the concentration of the ester-crosslinked hyaluronic acid dispersed in a physiologically acceptable medium is less than 1 mass %, no higher therapeutic effect than that of commercially available products will be obtained. Further, the hyaluronic acid molecules themselves have high affinity with water. Thus, when the ester-crosslinked hyaluronic acid is dispersed in a physiologically acceptable medium, it is not practicable to increase the hyaluronic acid concentration to be higher than 20 mass %, since the fluidity of the dispersion will be significantly impaired.

In the present invention, liquid (A) which is an aqueous solution containing a hyaluronic acid ester derivative and buffered to a pH of from 4.5 to 6.5, and liquid (B) which is an aqueous solution having such a buffering power that when it is mixed with the liquid (A), the mixed liquid has a pH within a range of from 6.8 to 7.8, are such that when the liquids (A) and (B) are finally mixed, they form a physiologically acceptable aqueous medium. Physiologically acceptable means that when the therapeutic agent for joints is injected into the articular cavity, the aqueous medium itself will not cause unfavorable effects or side-effects, such as swelling or contraction, or inflammation of the tissues. The physiologically acceptable aqueous medium is usually an aqueous solution of at least one low molecular weight substance selected from an inorganic salt such as a chloride, a sulfate, a phosphate or a bicarbonate of an alkali or an alkaline earth metal, for example, sodium chloride, sodium sulfate or magnesium chloride, or a corresponding potassium or calcium salt, a salt of an organic acid, such as sodium lactate or sodium acetate, and a neutral organic substance such as glucose, mannose or a polyhydric alcohol, for example, glycerol or mannitol. The type and the amount of the low molecular weight component have to be selected so that physiologically acceptable osmotic pressure, pH and ion content will be achieved when the liquids (A) and (B) are finally mixed.

The buffer component in the liquid (A) which is an aqueous solution containing a hyaluronic acid ester derivative and buffered to a pH of from 4.5 to 6.5, may optionally be selected from physiologically acceptable components which can buffer to a predetermined pH. For example, an organic acid salt such as acetic acid/sodium acetate, lactic acid/sodium lactate or citric acid/sodium citrate is suitable. Hyaluronic acid itself is also a high molecular electrolyte having carboxyl groups, and the buffering power of hyaluronic acid itself may also be effectively utilized.

The buffer component in the liquid (B) which is an aqueous solution having such a buffering power that when it is mixed with the liquid (A), the mixed liquid has a pH within a range of from 6.8 to 7.8, may optionally be selected from substances the use of which is certified as pharmaceutical additives, so that physiologically acceptable osmotic pressure, pH and ion content will be achieved when the liquids (A) and (B) are finally mixed. For example, when the buffer component in the liquid (A) is acetic acid/sodium acetate, when sodium hydroxide is selected as the buffer component in the liquid (B), sodium acetate will form when the liquids (A) and (B) are finally mixed.

In a case where the liquid (B) which is an aqueous solution having such a buffering power that when it is mixed with the liquid (A), the mixed liquid has a pH within a range of from 6.8 to 7.8, is an aqueous solution having hyaluronic acid dissolved therein, it has to be considered that hyaluronic acid itself is an unstable substance. Hyaluronic acid is prepared in the form of a sodium salt and is adapted, however, even sodium hyaluronate is not stable in the form of an aqueous solution. Further, hyaluronic acid has such properties that the higher the molecular weight, the poorer the stability. The stability of a solution of sodium hyaluronate is influenced by the pH, and the solution is relatively stable in the vicinity of neutral region. Accordingly, it is preferred to bring the pH of the liquid (B) itself to be at most 8.0, and to adjust the buffering power by the concentration of the buffer component. As the buffer component to adjust the pH to at most 8.0, a phosphate buffer component, a borate buffer component, a carbonate buffer component or an organic substance buffer component may, for example, be used. The concentration of hyaluronic acid dissolved is preferably within a range of from 0.5 to 2.0 mass % in view of effectiveness as the therapeutic agent for joints.

A stabilizer which improves the stability of hyaluronic acid itself may be added to the liquid (A) and also to the liquid (B) when hyaluronic acid is dissolved therein. The stabilizer which improves stability of hyaluronic acid itself is disclosed, for example, in JP-A-8-104642, JP-A-10-212303, JP-A-11-302197.

For example, a reducing agent containing iodine or a reducing agent containing sulfur is suitable since the stabilizer itself is not restricted by the pH. Further, since the stability of hyaluronic acid itself is significantly influenced by heavy metal ions of e.g. iron in some cases, it is also effective to add an agent which inactivates metals, such as phosphoric acid.

Now, practical storage form of the separate type medical material of the present invention will be described below.

In the practical form of storing the liquids (A) and (B) separately from each other, the liquid (A) is packed in a container as a suspension in which the ester derivative of hyaluronic acid after being ground is dispersed in a specific aqueous medium. The liquid (B) is packed in a separate container or in a separate compartment in the same container, so that it is not mixed with the liquid (A) during the storage. In general, when a product is provided as a pharmaceutical/medical material, it is packed in a syringe and supplied. For example, a two-pack type prefilled syringe fulfills the object, and it is preferred that the liquids (A) and (B) are separately enclosed in such a storage container. The position of the protrusion of the syringe for liquid passing, the position of the rubber stopper etc. are adjusted to optimum positions depending upon the enclosed amount and the volume ratio of the liquids (A) and (B). A container to which e.g. a static mixer is attached may be used for the purpose of improving the mixing properties of the liquids (A) and (B).

The static mixer may be attached to the syringe tip of a two-pack type prefilled syringe or to the mixing portion at the tips of two syringes into which the liquids (A) and (B) are separately packed.

The medical material to be used for treating joints of the present invention may contain a medicine or a pharmaceutically acceptable lubricant. As the medicine, a proper pharmaceutically active agent such as an anesthetic, an antibiotic, a steroidal or nonsteroidal anti-inflammatory agent, a hormone type anti-inflammatory agent such as somatostatin, epitheliotropic vitamin, cytokine such as IL-1 or IL-6, cytokine receptor, growth factor such as FGF, an antirheumatic drug, an antiallergic agent or an immunosuppressant agent, may be added.

As the lubricant, a phospholipid is suitable. In the present invention, phospholipids obtained by extraction from animal tissues or by artificial preparation may be used without any restriction on their source. The phospholipid is preferably phosphatidylcholine, phosphatidylethanolamine, phosphatidylserine, phosphatidylglycerol, phosphatidylinositol or sphingomyelin or a derivative thereof. Particularly preferred is α-dipalmitoylphosphatidylcholine (α-DPPC). The α-DPPC may be any of an L-form, a D-form and a racemic (DL) mixture.

The concentration of the phospholipid used in the present invention is preferably from 1 to 200 mg/ml. If the concentration of the phospholipid is less than 1 mg/ml, the effect tends to be low as a medicine for joints, and if it exceeds 200 mg/ml, agglutination of the phospholipid tends to be significant, and there will be troublesome in view of storage, and the handling tends to be difficult. Since the phospholipid is an amphipatic substance, it may be formed into liposomes for the purpose of stabilization in a hyaluronic acid solution, however, it may be merely suspended without formation into liposomes.

It is optional to add the medicine or the pharmaceutically acceptable lubricant to be added for the medical material to be used for treatment of joints of the present invention, either to the liquid (A) or the liquid (B) or to both liquids, depending upon the physicochemical properties of the medicine or the lubricant or the purpose of addition. Further, similarly, it is optional to add it to the inside of the dispersed particles of the ester derivative of hyaluronic acid in the liquid (A), to the dispersing medium or to both. For example, in a case where the dosage form is designed so that the concentration of the added medicine is kept constant in the articular cavity, that is, the DDS effect is obtained, it is desirable to add the desired medicine or lubricant to the inside of the dispersed particles of the ester derivatives of hyaluronic acid.

The form of the separate type medical material of the present invention may be a medical material for injection into joints, packed in a syringe.

EXAMPLES

Now, the present invention will be explained in further detail with reference to Examples. However, the present invention is by no means restricted to such specific Examples.

Example 1

Example of Production of Hyaluronic Acid Gel by Freezing/Thawing Method

Sodium hyaluronate (manufactured by DENKI KAGAKU KOGYO KABUSHIKI KAISHA, molecular weight $2 \times 10^6$ Da) was dissolved in distilled water to prepare a 1 mass % hyaluronic acid aqueous solution. The pH of this aqueous solution is adjusted to pH 1.5 with 1 mol/l hydrochloric acid (Wako Pure Chemical Industries, Ltd.). 15 ml of the acidic hyaluronic acid aqueous solution was put in a 30 ml glass bottle and placed in a refrigerator set at −20° C. for 65 hours and then thawed at 25° C. to obtain a spongy hyaluronic acid gel.

The gel was immersed in a 100 mmol/l phosphate buffer (pH 6.8) several times to completely neutralize the gel. Then, the obtained spongy hyaluronic acid gel was ground by a mixer to obtain a gel-ground suspension. The suspension was subjected to centrifugal separation at 3,000 rpm for 5 minutes to separate the gel content, to which a new buffer was added, and such an operation was repeatedly carried out at least 5 times to replace the gel solvent with a 5 mmol/l phosphate buffer-physiological saline.

A hyaluronic acid gel suspension produced by an acidic freezing/thawing method was obtained by the above method.

Example of Production of Hyaluronic Acid Gel by Acid Mixing Method 5 g of a powder of sodium hyaluronate (manufactured by DENKI KAGAKU KOGYO KABUSHIKI KAISHA, molecular weight $2\times10^6$ Da) was weighed, to which 15 ml of 1N nitric acid (Wako Pure Chemical Industries, Ltd.) which was cooled with ice was added. They were thoroughly mixed in a beaker, and the beaker was put in a plastic bag and placed in a refrigerator at 4° C. for 65 hours to obtain a spongy hyaluronic acid gel. The gel was immersed in a 100 mmol/l phosphate buffer (pH 6.8) several times to completely neutralize the gel. Then, the obtained spongy hyaluronic acid gel was ground by a mixer to obtain a gel-ground suspension. The suspension was subjected to centrifugal separation at 3,000 rpm for 5 minutes to separate the gel content, to which a new buffer was added, and such an operation was repeatedly carried out at least 5 times to replace the gel solvent with a 5 mmol/l phosphate buffer-physiological saline. A hyaluronic acid gel suspension produced by an acid mixing method was obtained by the above method.

The pH stability of the hyaluronic acid gels produced by the above methods was evaluated by the following accelerated test. For evaluation, gel suspensions adjusted to a hyaluronic acid concentration of 1 mass % in acetate buffer-physiological salines and phosphate buffer-physiological salines at pH 4, pH 5, pH 6 and pH 7, were used.

10 ml of each of the gel suspensions was put in a 15 ml plastic tube, left to stand on a warm bath at 60° C. and sampled every 2 hours. The sampled liquid was firstly subjected to centrifugal separation at 12,000 rpm for 5 minutes to remove the gel content, and then subjected to filtration by a filter of 0.22μ to completely remove the gel. The supernatant was subjected to GPC analysis and calorimetric analysis to obtain the hyaluronic acid concentration. The hyaluronic acid concentration in the supernatant is the concentration of the gel dissolved, and thus the proportion of the remaining gel and the proportion of the dissolved gel (the total of them corresponds to 100%) are obtained from the ratio to the initial concentration. The proportion of the remaining gel at each sampling time was obtained by the above method. The results are shown in Table 1.

TABLE 1

| | Gel remaining ratio (%) | | | |
|---|---|---|---|---|
| Hour | pH 4 | pH 5 | pH 6 | pH 7 |
| 0 | 100 | 100 | 100 | 100 |
| 2 | 99 | 99 | 99 | 98 |
| 4 | 98 | 99 | 98 | 97 |
| 6 | 97 | 99 | 96 | 95 |
| 8 | 95 | 99 | 96 | 93 |
| 10 | 95 | 98 | 94 | 89 |
| 12 | 93 | 97 | 93 | 89 |
| 14 | 93 | 97 | 92 | 89 |
| 16 | 90 | 97 | 90 | 87 |
| 25 | 88 | 95 | 84 | 75 |

As shown in Table 1, 25 hours after dissolution, the gel remaining ratio in the gel suspension adjusted to pH 7 was 75%, whereas 84% of the gel remained in the gel suspension adjusted to pH 6, and 88% of the gel remained in the gel suspension adjusted to pH 4. Further, at pH 5, so large as 95% of the gel remained, and it was found that the gel has storage stability at a low pH side in the vicinity of pH 5 with significance.

Example 2

Sodium hyaluronate (manufactured by DENKI KAGAKU KOGYO KABUSHIKI KAISHA, molecular weight $2\times10^6$ Da) was dissolved in distilled water to prepare a 1 mass % hyaluronic acid aqueous solution. The pH of this aqueous solution was adjusted to pH 1.5 with 1 mol/l hydrochloric acid (Wako Pure Chemical Industries, Ltd.). 100 ml of the acidic aqueous solution of hyaluronic acid was put in a 200 ml glass bottle and placed in a refrigerator set at −20° C. for 14 days and then thawed at 25° C. to obtain a spongy hyaluronic acid gel.

The obtained gel was immersed in a 100 mmol/l phosphate buffer (pH 6.8) several times to completely neutralize the gel. Then, the obtained spongy hyaluronic acid gel was ground by a mixer to obtain a gel-ground suspension. The suspension was subjected to centrifugal separation at 3,000 rpm for 5 minutes to separate the gel content. 1 l of distilled water was added to the gel content and washed with stirring. The centrifugal separation and washing of the gel content were repeated 5 times to completely remove the phosphate buffer component as a neutralizing agent. The hyaluronic acid concentration was brought to 5 mass % with physiological saline, and the pH was adjusted to 5.0 by adding hydrochloric acid, to obtain liquid (A). A 0.01 N sodium hydroxide aqueous solution was prepared to obtain liquid (B).

1.6 ml of the above liquid (B) was added to 10 ml of the liquid (A) adjusted to pH 5.0, followed by thorough mixing. The mixed aqueous solution had a pH of 7.4.

Example 3

Sodium hyaluronate (manufactured by DENKI KAGAKU KOGYO KABUSHIKI KAISHA, molecular weight $2\times10^6$ Da) was dissolved in physiological saline buffered to a pH of 8.0 with a 20 mM phosphate buffer, to obtain liquid (B). 8.0 ml of the above prepared liquid (B) was added to 2.0 ml of the liquid (A) prepared in Example 2, followed by thorough mixing. The mixed aqueous solution had a pH of 7.4.

Example 4

Sodium hyaluronate (manufactured by DENKI KAGAKU KOGYO KABUSHIKI KAISHA, molecular weight $2\times10^6$ Da) was dissolved in physiological saline buffered to a pH of 8.0 with a 20 mM borate buffer, to obtain liquid (B). 8.0 ml of the above prepared liquid (B) was added to 2.0 ml of the liquid (A) prepared in Example 2, followed by thorough mixing. The mixed aqueous solution had a pH of 7.4.

Example 5

Example of Production of Separate Type Medical Material Containing Hyaluronic Acid Gel by Freezing/Thawing Method Sodium hyaluronate (manufactured by DENKI KAGAKU KOGYO KABUSHIKI KAISHA, molecular weight $2\times10^6$ Da) was dissolved in distilled water to prepare a 1 mass % hyaluronic acid aqueous solution. The pH of the aqueous solution was adjusted to pH 1.5 with 1 mol/l hydrochloric acid (Wako Pure Chemical Industries, Ltd.). 15 ml of the acidic aqueous solution of hyaluronic acid was put in a 30 ml glass bottle and placed in a refrigerator set at −20° C.

After 65 hours, the aqueous solution was thawed at 25° C. to obtain a spongy hyaluronic acid gel. The gel was immersed in a 100 mmol/l phosphate buffer (pH 6.8) several times to completely neutralize the gel.

Then, the obtained spongy hyaluronic acid gel was ground by a cup mixer (12,000 rpm, 2 minutes) to obtain a gel-ground suspension. The suspension was subjected to centrifugal separation at 3,000 rpm for 5 minutes to separate the gel content, to which a new buffer was added, and such an operation was repeatedly carried out at least 5 times to replace the gel solvent with a 5 mmol/l acetate buffer-physiological saline having a pH of 5.

Liquid (A) which is a suspension (pH 5.0) of a hyaluronic acid gel suspended in an acetate buffer-physiological saline at a concentration of 2 mass %, and liquid (B) which is a solution of hyaluronic acid (manufactured by DENKI KAGAKU KOGYO KABUSHIKI KAISHA) dissolved in a phosphate buffer-physiological saline (pH 7.5) at a concentration of 1 mass %, were separately packed in a prefilled syringe (type G) manufactured by TOP CORPORATION in a proportion of (A):(B)=2:8. Namely, as shown in FIG. 1, 0.6 ml of the hyaluronic acid gel suspension as the liquid (A) was packed in a compartment (A) at the injection side, and 2.4 ml of the hyaluronic acid solution as the liquid (B) was packed in a compartment (B) at the plunger side.

Example 6

Example of Production of Separate Type Medical Material Containing Hyaluronic Acid Gel by Acid Mixing Method 5 g of a powder of sodium hyaluronate (manufactured by DENKI KAGAKU KOGYO KABUSHIKI KAISHA, molecular weight $2 \times 10^6$ Da) was weighed, to which 15 ml of 1 mol/l nitric acid (Wako Pure Chemical Industries, Ltd.) which was cooled with ice was added. They were thoroughly mixed in a beaker, put in a plastic bag and placed in a refrigerator at 4° C. for 65 hours to obtain a spongy hyaluronic acid gel. The gel was immersed in a 100 mmol/l phosphate buffer (pH 6.8) several times to completely neutralize the gel.

Then, the obtained spongy hyaluronic acid gel was ground by a cup mixer (12,000 rpm, 2 minutes) to obtain a gel-ground suspension. The suspension was subjected to centrifugal separation at 3,000 rpm for 5 minutes to separate the gel content, to which a new buffer was added, and such an operation was repeatedly carried out at least 5 times to replace the gel solvent with a 5 mmol/l acetate buffer-physiological saline having a pH of 5.

Liquid (A) which is a suspension (pH 5.0) of a hyaluronic acid gel suspended in an acetate buffer-physiological saline at a concentration of 2 mass %, and liquid (B) which is a solution of hyaluronic acid (manufactured by DENKI KAGAKU KOGYO KABUSHIKI KAISHA) dissolved in phosphate buffer-physiological saline (pH 7.5) at a concentration of 1 mass %, were separately packed in a prefilled syringe (type G) manufactured by TOP CORPORATION in a proportion of (A):(B)=2:8. Namely, as shown in FIG. 1, 0.6 ml of the liquid (A) as a hyaluronic acid gel suspension was packed in a compartment (A) at the injection side, and 2.4 ml of the liquid (B) as a hyaluronic acid solution was packed in a compartment (B) at the plunger side.

Comparative Example 1

Preparation of Non-Separate Type Mixed Medical Material of Hyaluronic Acid and Hyaluronic Acid Gel Liquid (A) which is a suspension (pH 5.0) of a hyaluronic acid gel suspended in acetate buffer-physiological saline at a concentration of 2 mass %, and liquid (B) which is a solution of hyaluronic acid (manufactured by DENKI KAGAKU KOGYO KABUSHIKI KAISHA) dissolved in phosphate buffer-physiological saline (pH 7.5) at a concentration of 1 mass %, were mixed in a proportion of (A):(B)=2:8, and then injected into a syringe (SS-02S2138) manufactured by TERUMO CORPORATION.

Example 7

Hyaluronic Acid Gel Stability in Hyaluronic Acid Preparation

Syringes prepared in Example 2 and Comparative Example 1 were kept in a thermostatic chamber at 60° C. The suspensions were taken out at each time for sampling. The sampled liquid was firstly subjected to centrifugal separation at 12,000 rpm for 5 minutes to remove the gel content, and then subjected to filtration by a filter of 0.22μ to completely remove the gel. The supernatant was subjected to GPC analysis and calorimetric analysis to obtain the hyaluronic acid concentration. The hyaluronic acid concentration in the supernatant increases by the concentration of the gel dissolved, and accordingly the proportion of the remaining gel and the proportion of the dissolved gel (the total of them corresponds to 100%) are obtained from the ratio to the initial concentration. The proportion of the remaining gel at each sampling time was obtained by the above method. The results are shown in Table 2.

TABLE 2

| | Gel remaining ratio (%) | | | | |
|---|---|---|---|---|---|
| | 0 hour | 10 hours | 15 hours | 20 hours | 25 hours |
| Ex. 1 | 100 | 99 | 98 | 97 | 94 |
| Comp. Ex. 1 | 100 | 90 | 85 | 70 | 64 |

As shown in Table 2, after keeping at 60° C. for 25 hours, in Comparative Example 1 in which the liquids were uniformly mixed, only 64% of the gel remained as compared with the amount at the beginning, whereas in Example 1 in which the liquids were separated, the gel remaining ratio was 94% as compared with the amount at the beginning and was significantly high. Thus, it was found that the stability of the gel is increased by storage in a separate form.

Example 8

Retention of Hyaluronic Acid Preparation in the Body

In order to evaluate effectiveness as a knee joint preparation, retention of the separate type medical material of hyaluronic acid gel and hyaluronic acid solution prepared in Example 5, in the rabbit knee articular cavity, was tested. The test was carried out in accordance with the following procedure. 0.25 ml of a mixed liquid of hyaluronic acid gel and hyaluronic acid solution (hyaluronic acid gel suspension: hyaluronic acid solution=2:8) was administered to left knees of three-month-old rabbits (Kbs:NZW male). One day and three days after the administration, the rabbits were anesthetized by intravenous administration of pentobarbital sodium to earlap and then killed by bleeding. Then, the leg to which the mixed liquid was administered was amputated, the knee joint was opened from the back, the cavity was washed out with physiological saline, and the liquid in the knee articular cavity was recovered. Further, with respect to the leg to which the mixed liquid was not administered, the same recovery was carried out. With respect to the obtained liquid in the articular cavity, the pH was adjusted to the alkali side to completely decompose the remaining hyaluronic acid gel, and then the total hyaluronic acid amount was quantitatively analyzed by GPC analysis. Then, employing the amount of hyaluronic acid in the liquid recovered from the knee to which the mixed liquid was not administered, as the background, correction was carried out to obtain the recovery rations of hyaluronic acid one day and three days after the administration.

As a result, the recovery rate of hyaluronic acid one day after the administration was 80%, and the recovery rate of hyaluronic acid three days after the administration was 50%.

Accordingly, it was found that hyaluronic acid administered to the articular cavity remained one day and three days after the administration, and effectiveness as a joint preparation was shown.

INDUSTRIAL APPLICABILITY

According to the present invention, a dispersed aqueous solution of a weakly acidic hyaluronic acid ester derivative and an aqueous solution of a neutralizing agent therefor, including a case where hyaluronic acid is dissolved in the aqueous solution of a neutralizing agent, are kept separately from each other so that they are under different pH conditions, to keep them in a state with excellent storage stability.

Such a preparation that liquids are kept separately from each other and mixed at the time of administration for treatment, so that they can be finally administered under a physiological neutral pH condition, can be provided.

According to the present invention, it is possible to satisfy both storage stability of a hyaluronic acid ester derivative and avoidance of irritation and pain at the time of injecting a therapeutic agent for joints, and it is possible to provide a hyaluronic acid ester derivative as a therapeutic agent for joints.

The invention claimed is:

1. A pair of compositions separately comprising:
   (A) an aqueous solution having a pH ranging from 4.5 to 6.5 containing a self-crosslinked hyaluronic acid, and
   (B) an amount of an aqueous buffer that when mixed with (A) produces an aqueous solution having a pH ranging from 6.8 to 7.8;
   wherein (A) and (B) are kept separately from each other.

2. The compositions of claim 1, wherein the self-crosslinked hyaluronic acid in (A) is present at a concentration ranging from 1 to 20 mass % of the total mass of (A).

3. The compositions of claim 1, further comprising wherein (B) has a pH of 8 at most.

4. The compositions of claim 1, further comprising a medical kit that contains separate containers of (A) and (B).

5. The compositions of claim 4, wherein (A) and (B) are contained in separate syringes.

6. The compositions of claim 1 which further comprise a pharmaceutically acceptable lubricant which may optionally be combined with either (A) or (B).

7. The compositions of claim 6, wherein the lubricant is dissolved or dispersed in (A).

8. The compositions of claim 6, wherein the lubricant is dissolved or dispersed in (B).

9. The compositions of claim 6, wherein said pharmaceutically acceptable lubricant is at least one selected from the group consisting of the phospholipids phosphatidyl choline, phosphatidylethanolamine, phosphatidylserine, phosphatidylglycerol, phosphatidylinositol, sphingomyelin, and α-dipalmitoylphosphatidylcholine (α-DPPC).

10. A third composition having a pH ranging from 6.8 to 7.8 produced by mixing components (A) and (B) of the compositions of claim 1 at the time of treatment.

11. The compositions of claim 1, further comprising wherein (A) has a pH ranging from 4.0 to 6.0.

12. A method for treating a subject in need thereof and having an arthropathy comprising:
   mixing at the time of treatment sufficient amounts of (A) and (B) from the compositions of claim 1 to produce a third composition having a pH ranging from 6.8 to 7.8, and
   administering said third composition into a joint of said subject.

* * * * *